United States Patent [19]

Galaj et al.

[11] Patent Number: 5,371,182

[45] Date of Patent: Dec. 6, 1994

[54] SELF-DOPED CONDUCTIVE POLYANILINES, AND METHOD OF PREPARING THEM

[75] Inventors: Stanislas Galaj, Arcueil; Alain Le Méhauté, Gif Sur Yvette, both of France

[73] Assignee: Alcatel N.V., Amsterdam, Netherlands

[21] Appl. No.: 961,691

[22] PCT Filed: May 6, 1992

[86] PCT No.: PCT/FR92/00411

§ 371 Date: Jun. 11, 1993

§ 102(e) Date: Jun. 11, 1993

[87] PCT Pub. No.: WO92/19666

PCT Pub. Date: Nov. 12, 1992

[30] Foreign Application Priority Data

May 7, 1991 [FR] France .................. 91 05578

[51] Int. Cl.⁵ .............................. C08G 73/00
[52] U.S. Cl. .................... 528/422; 528/391; 528/399; 525/540
[58] Field of Search ............ 528/422, 391, 399; 525/540

[56] References Cited

U.S. PATENT DOCUMENTS

| | | | |
|---|---|---|---|
| 4,806,271 | 2/1989 | Yaniger et al. | 252/500 |
| 4,940,517 | 7/1990 | Wei | 204/78 |
| 5,069,820 | 12/1991 | Jen et al. | 252/500 |

FOREIGN PATENT DOCUMENTS

| | | |
|---|---|---|
| 0128272 | 12/1984 | European Pat. Off. . |
| 0210023 | 1/1987 | European Pat. Off. . |
| 0345693 | 12/1989 | European Pat. Off. . |
| 2152889 | 1/1973 | France . |
| 2554822 | 5/1985 | France . |
| WO8901694 | 2/1989 | WIPO . |

OTHER PUBLICATIONS

Haney et al, *Synthetic Metals*, 31 (1989) pp. 369–370.
Alix et al., *Synthetic Metals*, 29 (1989) pp. E457–462.
Heath's *Standard French and English Dictionary*, Part I, p. 714 (1962).
The Handbook of Chemistry and Physics, (46$^{th}$Edition), p. D-75.
Nebergall et al, *General Chemistry*, D. C. Heath and Company (4$^{th}$Edition), pp. 453–461.
Lancaster Chemical Catalog, pp. 222 and 1072.

*Primary Examiner*—John Kight, III
*Assistant Examiner*—Terressa Mosley
*Attorney, Agent, or Firm*—Sughrue, Mion, Zinn, Macpeak & Seas

[57] ABSTRACT

The present invention relates to self-doped conductive polyanilines and to a method of preparing them. The benzene and/or quinone rings of said polyanilines can be functionalized graft chains or substituents corresponding to the formula:

$$-A-Z$$

in which:

A is a hydrocarbon radical having 2 to 8 atoms of carbon interrupted by at least 1 hetero atom; and Z is a strong acid function or a salt thereof.

22 Claims, 3 Drawing Sheets

SELF-DOPED CONDUCTIVE POLYANILINES, AND METHOD OF PREPARING THEM

The present invention relates to self-doped conductive polyanilines, a method of preparing them, and their application to the field of electromagnetism. It also relates to preparing one of the materials used in obtaining said polyanilines.

Polyaniline is a polymer whose monomer units correspond to the formula:

in which n lies in the range 0 to 1.

Two types of ring are present in polyaniline: benzene rings and quinone rings corresponding to different oxidation states represented by the variable n. In practice, three types of polyaniline are considered: the reduced form, the semioxidized form, and the oxidized form. The reduced form corresponds to 100% benzene rings (n=1), the semi-oxidized form corresponds to 75% benzene rings and 25% quinone rings (n=0.5), and the oxidized form corresponds to 50% benzene rings and 50% quinone rings (n=0). Nevertheless, the distribution and the periodicity of benzene and quinone rings along the chain is statistical. The oxidation ratio is controlled by the quantity of oxidizer added to the polymerization reaction medium.

It so happens that the semi-oxidized form, known as "polyemeraldine" and possessing as many amine groups (N—H) as imine groups (—N=), is the form which becomes the most highly conductive after hydrogen acid fixation; this operation is called "doping".

Conduction is thus obtained when the polyaniline corresponds to H+ doping. The polymer is thus conductive while the backbone is protonated. This doping is reversible, but not very stable against possible deprotonation, e.g. by washing in water or by heat treatment that evaporates the hydrogen acid.

In order to stabilize the conductivity of such polymers, proposals have been made to dope them by grafting. However, the presence of too high a number of side chains reduces conductivity by reducing contact zones between chains. The problem thus arises of the regularity with which the grafted chains are positioned so as to avoid having too high a density of grafted chains per unit length at some particular point along the chain, since that impedes conduction.

The grafting was initially performed by the action of a dopant on non-conductive polyanilines (Patent WO-8 901 694). The amine or imine sites, corresponding respectively to the benzene rings and to the quinone rings, are the sites affected by known grafting. Such grafting thus takes place only on the nitrogen atoms, and not on the rings. For example, U.S. Pat. No. 4,806,271 describes the grafting of an alkyl chain or an aryl chain with a terminal function onto the nitrogen atom. When the imine sites of the chain are grafted, they can no longer fix protons, which condition is necessary for good conductivity.

Conductive polyanilines with improved stability against deprotonation can be obtained by "self-doping", i.e. by introducing an acid function that is securely bonded to the chain.

Self-doped polyanilines obtained by alkylation of the nitrogen atom by means of chains carrying a terminal sulfonic acid function have been described (Synthetic Metals, 31 (1989), pp. 369–378). A subsequent treatment is performed on a standard polyaniline. Under such circumstances the grafting is likewise performed on the nitrogen atom.

Research efforts have thus been directed to obtaining polyanilines that are grafted on the rings, which can be achieved only by polymerizing monomers having rings that already carry acid functions.

However, polyanilines carrying short grafted chains on their rings present no differences in physico-chemical characteristics over non-doped polyanilines, in particular with respect to chain conductivity. If the polyaniline is treated with oleum, a fraction of the rings are grafted with —SO$_3$H, which leads to a small increase in conductivity, up to a level close to $10^{-3}$ S.cm$^{-1}$ (Mol. Liq. Cryst. 189 (1990) 255).

A polymer obtained from a monomer having a grafted chain on its ring carrying a proton donor function (—COOH) has been described in U.S. Pat. No. 4,940,517, however that function is quite insufficient for doping the polymer. In addition, the homopolymerization method limits the length of usable grafted chain.

It is known that it is very difficult to polymerize monomers carrying a group of substantial size (at least three links) in a conventional polymerization medium (e.g. HCl/(NH$_4$)$_2$S$_2$O$_8$) because of the steric hindrance which limits head-to-tail polymerization except in special media, e.g. HF—NH$_4$F at the eutectic point, using an electrochemical method (Synthetic Metals, 29 (1989), pp. 1377, 1382).

Finally, it is not possible with the above-described methods to vary the conductivity of the polymer in controlled manner as a function of the value which it is desired to obtain.

The technical problem which the invention sets out to solve is that of producing and obtaining a new class of conductive polyanilines which have improved characterization and conductive properties over polyanilines as prepared in the past, and in particular in which the propagation parameters of electromagnetic impedance Z and the propagation constant are more advantageous than those of prior art polyanilines. The said polyanilines also possess the advantage of being highly stable against possible deprotonation under the effects of water or a rise in temperature.

The present invention provides self-doped conductive polyanilines, characterized in that the benzene and/or quinone rings of these polyanilines carry functionalized grafted chains or substituents corresponding to the formula: in which:

A is a hydrocarbon radical having 2 to 8 atoms of carbon interrupted by at least one hetero atom; and Z is a strong acid function or a salt thereof.

Preferably the said —A— group is a hydrocarbon radical having 2 to 8 carbon atoms interrupted by at least one hetero atom selected from O and S. For example, the oxygen atom exerts a donor effect which stabilizes the positive charge of the main chain.

In a first implementation of polyanilines of the invention, said —A— group is selected from the group of residues having an ether or a polyether function, such as those corresponding to the formula: —O—(CH$_2$)$_n$—, —(CH$_2$O)$_n$— where n is greater than or equal to 2; —CH$_2$—O—(CH$_2$)$_n$—, —(CH$_2$—CH$_2$O)$_n$— with n greater than or equal to 1; or having an ester function such as $-COO-(CH_2)_n-$, $-CH=CH-COO-(CH_2)_n-$ with n greater than or equal to 1.

In another implementation of polyanilines of the invention, the said $-A-$ group includes an oxygen atom in its chain and corresponds to the formula:

$$-(CH_2)_r-O-(CH_2)_s-$$

in which:
r is an integer equal to 0 or 1; and
s is an integer equal to 3 or 4.

In another embodiment of polyanilines of the invention, said $-Z-$ group is a strong acid function selected from residues of sulfonic, phosphonic, and phosphoric acids and salts thereof.

The sulfonic acid function is the preferred function. Salts such as metal salts are also envisaged. The preferred salts are alkali salts (Na, K . . . ).

In another embodiment of polyanilines of the invention, their backbones correspond to the backbone of polyemeraldine.

Advantageously, the number of functionalized grafted chains is equal to one-half the number of benzene and/or quinone rings, which leads to maximum conductivity. This may be achieved by adjusting the relative proportions of each of the monomers.

For example, if the monomer A molecule carries only one substituent, maximum polymer conductivity is obtained by equimolecular incorporation of monomer A and monomer B; in contrast, if monomer A carries two substituents, then only one molecule of monomer A should be incorporated for three molecules of monomer B.

Also, their conductivity can be varied by varying the molecular ratio of monomer A to monomer B. For example, by reducing the proportion of monomer A relative to monomer B, it is possible to lower conductivity since the number of functionalized grafted chains is reduced relative to the total number of rings.

The present invention also provides a method of preparing self-doped conductive polyanilines comprising a step of copolymerizing two monomers in an acid medium and in the presence of an oxidizer, one of the monomers being functionalized and the other being non-functionalized, and having the following formulas A and B respectively:

in which:
q is 0 or 1;
p is 0 or 1;
$R_1$ and $R_2$ are equal or different and are groups of the $-A-Z$ type in which $-A-$ is a hydrocarbon containing a radical having 2 to 8 atoms of carbon and interrupted by at least 1 hetero atom, and $-Z$ is a strong acid function or a salt thereof;

R and R' are identical or different, with the dashed lines indicating that R and/or R' is/are bonded either to the nitrogen atom or the ring;

when bonded to the ring, they are, by way of non-limiting example: $-H$, $-OH$, an alkyl radical containing 1 to 12 atoms of carbon, or one of the following groups: $-CH_2OH$, $-C_2H_4OH$, $-COOH$, $-OCH_3$, $-OC_2H_5$;

when they are attached to the nitrogen atom, they are $-H$, $-OH$, an alkyl radical, a phenyl radical, or one of the following groups: $-CH_2OH$, $-C_2H_4OH$, $-COOH$.

The groups R and R' are selected to ensure compatibility with the matrix for making composites.

The copolymerization includes an induction stage during which the oxidizer is present in small quantity in the copolymerization medium, and a production stage.

The term "induction stage" corresponds to the period during which the reaction is initiated, for example by applying heat or photochemically. The term "production stage" corresponds to the period of time during which polymer growth takes place.

In an implementation of the method of the invention, said monomer A is fully present in the reaction medium at the beginning of the reaction, and monomer B and the oxidizer are added in increments or continuously during the period of the induction stage and of the production stage, the fixed ratio of monomer B to oxidizer being substantially constant.

In another implementation of the method, said monomer B is also present in the copolymerization medium during the induction stage.

In yet another implementation of the method, said monomers A and B are fully present in the reaction medium at the beginning of the reaction, and the oxidizer is added in increments continuously over the period of the induction stage and of the production stage.

In yet another implementation of the method of the invention, the reaction medium is subjected during the induction stage to heating leading to a temperature that may reach 40° C. for several minutes, after which the temperature of the reaction medium is allowed to change under its own inertia.

The polymerization medium is any solvent that is inert to the reagents, e.g. water. The term "acid medium" is used to mean that the pH is less than 1. Suitable acids that may be mentioned include hydrochloric acid, sulfuric acid, phosphoric acid, etc., mixtures thereof, and the eutectic $HF-NH_4F$. The preferred acid is sulfuric acid. The term "oxidizing medium" is used to designate a medium containing an oxidizer that may be $KIO_3$, $H_2O_2$, $(NH_4)_2S_2O_8$, $(NH_4)_2Cr_2O_7$, etc. The oxidizer that is preferably used consists of $(NH_4)_2S_2O_8$ or $KIO_3$.

The said monomer B may be the dimer N-phenyl-p-phenylenediamine or aniline non-substituted or substituted on the ring or on its nitrogen by a group selected from: $-OH$, $-CH_2OH$, $-C_2H_4OH$, $-COOH$, alkyl, $-OCH_3$, and $-OC_2H_5$. The preferred monomer B is aniline. The monomer B may be a mixture.

Said monomer A is aniline mono- or di-substituted on the ring in the ortho position or in the meta position, of the type (o)$R_1$-aniline, (m)$R_1$-aniline, (o)$R_1$, (o)$R_2$-aniline, (o)$R_1$, (m)$R_2$-aniline, (m)$R_1$, (o)$R_2$-aniline, (m)$R_1$, (m)$R_2$-aniline, and mixtures thereof.

As an example of the group $R_1$ (and/or $R_2$), mention may be made of the following: $-C=CH-COO-(CH_2)_3SO_3H$; $-CH=CH-COO-(CH_2)_4SO_3H$; $-COO(CH_2)_3SO_3H$; $-COO(CH_2)_4SO_3H$; $-O(CH_3)_3SO_3H$; $-O(CH_2)_4SO_3H$; $-CH_2O(CH_2)_3SO_3H$; $-CH_2O(CH_2)_4SO_3H$; and sodium, potassium, or ammonium salts thereof.

The group $R_2$ should be selected so as to ensure compatibility with the matrix for making composites.

The said monomer A is preferably ortho disubstituted aniline.

During the polymerization operation, the association of two monomers can lead to the formation of carcinogenic benzidine:

which does not happen when each of the monomers carries two substituents in the ortho position, for reasons of steric hindrance.

The said monomer A preferably carries a sulfonic acid function. The introduction of a sulfonic acid function on an arylamine ring suppresses genotoxic activity in most cases.

The present invention also provides polyanilines obtained by the above-described method.

In a preferred implementation, the polyanilines are obtained from aniline as monomer B and aniline that is ortho or meta substituted by a group having the formula:

in which
  r is 0 or 1;
  s is 3 or 4;
or the corresponding alkali salt.

The particularly preferred polyanilines are obtained from aniline as monomer B and as monomer A: either 3-(3-aminobenzyloxy-1-propanesulfonic acid, or 4-(2-aminophenoxy)-1-butanesulfonic acid, or the sodium salts thereof.

The present invention also relates to a method of preparing type A monomers used for obtaining said polyanilines, which method, starting from an aromatic nitrated derivative carrying at least one hydroxyl or hydroxylated group in the ortho position or the meta position, consists:

in obtaining the metallic derivative of said derivative (alcoholate, phenolate);
  reacting it with a sultone in a medium that is anhydrous, polar, and apronic;
  reducing the nitro function into an amino function; and recovering the final product in the form of an internal salt or any salt derivative as a function of convenience in separation;
using the following reaction scheme:

The dashed lines mean that the substituent may be in the ortho position or in the meta position.

Each of these forms may be used directly for polymerization in an acid medium in the presence of an oxidizer.

Thus, for example, the hydroxylated and nitrated derivative may be selected from: orthonitrophenol, metanitrophenol, orthonitrobenzyl alcohol, metanitrobenzyl alcohol, 2-nitroresorcinol, 3-nitrocinnamic acid, etc. In the presence of NaOH or $CH_3ONa$, the derivative gives rise to the metal salt which reacts with a sultone, which may be selected from 1,3-propanesultone and 1,4-butanesultone. The monomer A is then obtained by reduction, e.g. by means of hydrazine, in the presence of Raney nickel as a catalyst.

In another implementation, said type A monomers are prepared from an amine-containing derivative carrying at least one hydroxyl group or group that is hydroxylated in the ortho position or in the meta position, using a method which consists:

in obtaining the metallic derivative of said derivative (alcoholate, phenolate);
  in reacting it with a sultone in a medium that is anhydrous, polar, and aprotic; and
  in recovering the final product in the form of an internal salt or of any salt derivative as a function of separation convenience, using the following reaction scheme:

The dashed lines indicate that the substituent may be in the ortho position or in the meta position.

Each of these forms may be used directly for polymerization in an acid medium in the presence of an oxidizer.

Thus, for example, the hydroxylated and amine-containing derivative may be selected from: orthoaminotrophenol; metaminophenol; orthoaminobenzyl alcohol; metaaminobenzyl alcohol; 2-aminoresorcinol; 3-aminocinnamic acid; etc.

The self-domed conductive polyanilines obtained by this method are put into solution in a solvent. The said solvent may be a basic aqueous solution such as a solution of sodium hydroxide or of potassium hydroxide, an organic basic solution, and preferably a volatile weak base such as ammonia, monomethylamine, dimethylamine, trimethylamine, monoethylamine, diethylamine, triethylamine, pyrrolidine, or pyridine. Preferably, self-doped polyanilines obtained by this method are put into solution in ammonia. Simple heat treatment serves to regenerate the self-doped polymer, e.g. in the form of thin layers or deposits on a plane surface or in a porous body.

The present invention also relates to electromagnetic applications of the above-mentioned polyanilines. These polyanilines may be used in a large number of fields, for example the field of semiconductive screening or electromagnetic shielding, or the microwave field.

Other characteristics and advantages of the present invention appear from the following description of implementations given by way of non-limiting illustration, and with reference to the accompanying drawings, in which.

EXAMPLE 1

Preparation of monomer A1

The following are introduced into an Erlenmeyer flask surmounted by a refrigerant and by a water vapor trap: 15.3 grams (g) of 3-nitrobenzyl alcohol (0.1 moles); 100 ml of toluene; and 12 g of anhydrous sodium carbonate in fine powder form. The suspension is stirred and reflux-heated for 24 hours. 13.5 g of 1,3-propanesultone is added and reflux heating is maintained for 8 hours.

The suspension is evaporated under vacuum and the residue is dissolved in 150 ml of water. 20 g of iron powder and 10 ml of concentrated hydrochloric acid are added to said solution. The suspension is stirred and heated to about 80° C. over 1 hour and then filtered. Sodium hydroxide is added to the filtrate and filtering is performed again to eliminate the abundant precipitate of iron hydroxides. The filtrate is acidified with HCl and then evaporated under a vacuum. The residue is taken up hot by anhydrous ethanol and then the suspension is filtered to eliminate the NaCl. Evaporation of the filtrate under a vacuum leaves a viscous residue that crystalizes partially after a few days. The crystals are dried and recrystalized in methanol.

The pale pink powder obtained has a mass of 8.3 g. The overall yield is 34%.

3-(3-aminobenzyloxy)-1-propanesulfonic acid is thus obtained having the following structural formula:

whose NMR spectrum (60 MHz in DMSO-$d_6$) is as follows:

a: wideband between 8.7 ppm and 10.6 ppm
b: 7.5 ppm (triplet) 7.3 ppm (multiplet)
c: 4.5 ppm (singulet)
d: 3.5 ppm (triplet)
e: 1.9 ppm (multiplet)
f: 2.5 ppm (multiplet).

EXAMPLE 2

Preparation of the monomer A2

30.9 g of 2-nitrophenol at 10% humidity (0.2 moles) are dissolved hot in 150 ml of water containing 8.2 g of sodium hydroxide. The solution is evaporated under a vacuum with a progressive rise in temperature to 110° C. The resulting anhydrous red crystals are dissolved in 150 ml of anhydrous dimethylsulfoxide containing 31.3 g of 1,4-butanesultone (0.23 moles). This solution contained in a sealed flask is placed in an oven at 90° C. for a length of time that may be as much as 48 hours. The solution is then concentrated under a vacuum, and then by adding 1-propanol and cooling, crystals of sodium 4-(2-nitrophenoxy)-1-butanesulfonate are precipitated.

The crystals are dried and then dissolved in a mixture comprising 200 ml of water and 100 ml of ethanol. This solution is heated to about 60° C.–70° C. 30 ml of hydrazine hydrate are added thereto, together with about 1 g to 2 g of Raney nickel in powder form: reduction of the nitro function begins. Two further additions of about 1 g of Raney nickel are performed at 30 minute intervals.

The solution is then boiled for 20 minutes. After cooling, the suspension is filtered and the filtrate evaporated under vacuum. The resulting residue is redissolved hot in a mixture of 1-propanol and water (95 to 5 by volume). After cooling, crystals precipitate. They are dried at 60° C. under a vacuum for 24 hours, thereby giving rise to a pale pink powder having a mass of 41.4 g. The overall yield is 70%.

Analysis shows that the powder is sodium 4-(2-aminophenoxy)-1-butane-sulfonate hydrated with 1.5 water molecules. This salt can be used directly in obtaining "self-doped" polyanilines.

The formula of the A2 monomer is:

and its NMR spectrum (60 MHz in DMSO-$d_6$) is as follows:
- a: 4.6 ppm (multiplet)
- b: 6.6 ppm (multiplet)
- c: 3.9 ppm (multiplet)
- d: and e: 1.7 ppm (multiplet)
- f: 2.4 ppm (multiplet)
- g: 3.3 ppm (singulet).

Another way of making the monomer A2 in larger quantity:

309 g of 2-nitrophenol at 10% humidity (2 moles) are dissolved hot in an Erlenmeyer flask containing 1 liter of water and 82 g of sodium hydroxide in pellets. This solution is evaporated under a vacuum progressively raising its temperature to 95° C. 700 ml of anhydrous dimethylsulfoxide and 313 g of 1,4-butanesultone are added to the resulting anhydrous red crystals. The mixture is heated progressively to 90° C. This temperature is maintained for 24 hours and then the orange-colored solution is concentrated under a vacuum by distilling a large fraction of the DMSO. 1 liter of water, 12 g of sodium hydroxide, and 50 ml of hydrazine hydrate are added to the resulting greenish residue. The solution is raised to about 70° C. and is then maintained at that temperature. About 2 g of Raney nickel are added and reduction begins. 50 ml of hydrazine hydrate and about 2 g of Raney nickel are added on six occasions at 30 minute intervals. Half an hour after the last addition, the suspension is boiled for 2 hours, cooled, and filtered. The residue obtained after evaporating the filtrate under a vacuum is redissolved hot in 2 liters of a mixture comprising 1-propanol and water (95 to 5 by volume). The solution is allowed to stand for 3 days at about 10° C. The resulting crystals are dried, washed in anhydrous ethanol, and dried under a vacuum at 50° C. for 3 days. The mass of the resulting powder is 434.5 g. The overall yield is 74%.

EXAMPLE 3

Preparation of the monomer A3

309 g of 2-nitrophenol at 10% humidity (2 moles) are dissolved hot in an Erlenmeyer flask containing 1 liter of water and 82 g of sodium hydroxide in pellets. This solution is evaporated under a vacuum, progressively raising its temperature to 95° C. 350 ml of anhydrous dimethylsulfoxide and 270 g of 1,3-propanesultone are added to the anhydrous red crystals and a water vapor trap is installed on the flask. The mixture is heated progressively to 90° C. This temperature is maintained for 24 hours and the orange-colored solution is concentrated under a vacuum by distilling a large fraction of the DMSO. The yellowish residue is redissolved hot in a mixture constituted by 1.5 liters of ethanol, 1 liter of water, and 8 g of sodium hydroxide. The solution is raised to about 70° C., and is then maintained at that temperature. 50 ml of hydrazine hydrate and about 2 g of Raney nickel are added thereto, and reduction begins. Seven further additions each comprising 50 ml of hydrazine hydrate and about 2 g of Raney nickel are performed at 30 minute intervals. The reduction is practically over when the yellow-colored foam becomes white. Half an hour after the last addition, the suspension is boiled for 1 hour, then hot filtered. After the filtrate has been cooled, white crystals are deposited. They are dried, washed in ethanol, and then dried under a vacuum at ambient temperature initially, and then at 50° C. for 3 days. The mother liquors are hot concentrated under a vacuum so as to recover the balance of the product which is treated like the first batch. The mass of the resulting powder is 200.8 g for the first batch and 264.5 g for the second batch (less pure). The overall yield of this synthesis is 83%. The NMR spectrum (60 MHz in DMSO-$d_6$) shows that it comprises sodium 3-(2-aminophenoxy)-1-propanesulfonate hydrated with 1.5 molecules of water:

and its NMR spectrum (60 MHz in DMSO-$d_6$) is as follows:
- a: 4.6 ppm (singulet)
- b: 6.6 ppm (multiplet)
- c: 4.0 ppm (triplet)
- d: 2.0 ppm (multiplet)
- e: 2.6 ppm (triplet)
- f: 3.4 ppm (singulet).

EXAMPLE 4

Preparation of monomer A4

50 g of 3-nitrophenol (about 0.36 moles) are dissolved hot in 200 ml of water containing 14.75 g of sodium hydroxide. This solution is evaporated under a vacuum while progressively raising its temperature to 100° C. The resulting anhydrous red crystals are dissolved in 70 ml of anhydrous dimethylsulfoxide containing 54 g of 1,4-butanesultone. This solution is put in a sealed flask, and placed in an oven at 90° C. for 48 hours. Dimethylsulfoxide is evaporated under a vacuum. The pale yellow residue is redissolved hot in a mixture constituted by 300 ml of ethanol, 180 ml of water, and 1.5 g of sodium hydroxide. The solution is raised to about 70° C. 75 ml of hydrazine hydrate and about 2 g of Raney nickel are added thereto and reduction begins. Reduction is practically completed after 15 minutes when the yellow-colored foam becomes white. The suspension is boiled for 1 hour and then hot-filtered under a vacuum, with 600 ml of ethanol being added to the filtrate. After the filtrate has cooled, white crystals are deposited. They are dried, washed in ethanol, and then dried under a vacuum at ambient temperature initially and subsequently at 50° C. for 2 days. The mass of the resulting powder is 72.3 g. The overall yield is 75%.

The NRM spectrum (60 MHz in DMSO-$d_6$) shows that the product is anhydrous sodium 4-(3-aminphenoxy)-1-butanesulfonate:

and its spectrum is as follows:
- a: 5 ppm (singulet)
- b: 6.1 ppm (multiplet) 6.9 ppm (triplet)
- c: 3.8 ppm (multiplet)
- d: and e: 1.7 ppm (multiplet)
- f: 2.4 ppm (triplet).

EXAMPLE 5

Preparation of monomer A5

50 g of 3-nitrophenol (about 0.36 moles) are dissolved hot in 200 ml of water containing 14.75 g of sodium hydroxide. This solution is evaporated under a vacuum while progressively raising its temperature to 100° C. The resulting anhydrous red crystals are dissolved in 70 ml of anhydrous dimethylsulfoxide containing 48.4 g of 1,3-propanesultone. This solution is put in a sealed flask and placed in an oven at 90° C. for 48 hours. The dimethylsulfoxide is evaporated under a vacuum. The pale yellow residue is redissolved hot in a mixture constituted by 300 ml of ethanol, 180 ml of water, and 1.5 g of sodium hydroxide. The solution is raised to about 70° C. About 2 g of Raney nickel are added thereto; 75 ml of hydrazine hydrate are then added drop-by-drop and reduction begins. Reduction is practically terminated after 30 minutes when the yellow foam becomes white. The suspension is boiled for 1 hour, and then filtered under a vacuum after cooling. The filtrate is evaporated and the residue taken up hot by 600 ml of a water and ethanol mixture (95 to 5). After cooling the filtrate, white crystals are deposited. They are dried, washed in ethanol, and then dried under a vacuum at ambient temperature initially and then at 50° C. for 2 days. The mass obtained is 54 g.

In this way, the sodium salt of 3-(3-aminophenoxy)-1-propanesulfonic acid is obtained.

EXAMPLE 6

Preparation of monomer A6

Example 2 is repeated but starting from 0.2 moles of 2-nitroresorcinol, 16.4 g of sodium hydroxide, and 62.6 g (0.46 moles) of sodium 1-butanesulfonate. The sodium salt of 1-amino-2,6-bis(4-sulfobutoxy)benzene is obtained.

EXAMPLE 7

Copolymerization of monomers A1 and B

A1: 3-(3-aminobenzyloxy)-1-propanesulfonic acid B: aniline.

Mode of operation

A mixture constituted by 1.30 g of monomer A1, 0.5 g of monomer B, 10 ml of water, and 2.5 ml of sulfuric acid at 96% is stirred at ambient temperature. 2.5 g of ammonium peroxodisulfate in powder form is then added thereto in small pinches over about 30 minutes. The temperature rises by about 10° C. to 15° C. Stirring is continued for 2 hours. The resulting suspension is filtered and washed in water several times until the filtrate has a pH of about 7. The resulting sticky and blackish mass is dried under a vacuum for 24 hours at 60° C. The resulting copolymer is in the form of a fine dark green powder having a mass of 0.955 g.

A1 and B were used at an excess of about 20% relative to the stoichiometric quantity of oxidizer required for obtaining a copolymer whose backbone is that of polyemeraldine. The yield calculated using the oxidizer as the reference is 65%.

EXAMPLE 8

(Comparison)

Homopolymerization of A1 performed under the same conditions as the copolymerization of A1+B as described in Example 7 gives rise to a powder having a dark green-brown color with a yield, calculated relative to the oxidizer, of 30%.

EXAMPLE 9

(Comparison)

On its own, the aniline polymerizes into polyemeraldine with yields of about 80%.

EXAMPLE 10

Copolymerization of monomers A2 and B (A2)            (B)

A2: 4-(2-aminophenoxy)-1-butanesulfonic acid
B: aniline

Mode of operation

A mixture constituted by 5.35 g of monomer A2 in the form of hydrated sodium salts, 80 ml of water, and 20 ml of sulfuric acid at 96% is stirred at ambient temperature. 0.2 ml of monomer B and 1 g of ammonium peroxodisulfate is added thereto once every 10 minutes on eight occasions. A ninth addition corresponds to the remainder of the reagents: 1.7 ml of monomer B and 9.7 g of $(NH_4)_2SO_8$ are thus added in all. A2 and B are in excess by 10% relative to the stoichiometric quantity of oxidizer necessary for obtaining a copolymer whose backbone is that of polyemeraldine.

A small amount of heating is required (about 30° C. to 40° C.) to accelerate the copolymerization process since nothing happens after the second addition as can be seen from the very small change in the color of the reaction medium. Stirring is continued for 1 hour after the last addition. The almost black dark green suspension is very difficult to filter because it is quite viscous. It is preferable to dilute it in 500 ml of water and then to centrifuge it. The residue is redispersed in 200 ml of water and centrifuging is performed again. This operation is repeated one more time. The residue constituted by moist copolymer is practically completely free of foreign ions. Drying for 24 hours under a vacuum at 60° C. gives a nearly black dark green powder having a mass of 2.35 g.

The yield calculated with reference to the quantity of oxidizer is 41%.

The polymer obtained by copolymerization of 4-(2-aminophenoxy)-1-butanesulfonic acid (A2) with aniline is partially soluble in water under neutral conditions, and adding acid causes a portion of it to be reprecipitated. In both cases the solutions are green. It is totally soluble in a basic medium (sodium or ammonium hydroxide). The solutions obtained in this way are violet. Hot evaporation the ammonia solution provides green-colored conductive thin films.

Although the imine functions and the amine functions in the chain are less basic than ammonia, simple heat treatment displaces the equilibrium point and enables self-doped polyemeraldine to be regenerated.

In contrast, evaporating the sodium solution does not allow the conductive polymer to be regenerated as can be seen from the violet color of the resulting film.

EXAMPLE 11

A solution composed of 100 g of ammonium bichromate, 60 ml of 96% sulfuric acid, and 540 ml of water is added drop-by-drop over a period of 15 hours to a 2-liter Erlenmeyer flask containing a mixture of 150 mg of monomer A2 in the form of its hydrated sodium salts, 49 g of aniline, 90 ml of 96% sulfuric acid, and 820 ml of water. The reaction medium is kept at about 25° C. The viscous suspension is centrifuged. The residue is redismersed in 2 liters of water having 50 ml of acetic acid added thereto, and is then centrifuged. A "dark green" colored copolymer is obtained. This operation is repeated three more times and then the residue is dried under a primary vacuum at 60° C. The mass of powder obtained is 83.9 g. The yield calculated relative to the oxidizer is 64%.

EXAMPLE 12

Copolymerizating monomers A1 and B (A6)            (B)

A6: 1-amino-2,6-bis(4-sulfobutoxy)benzene
B: aniline

Mode of Operation

Example 10 is repeated but starting from 4.5 of monomer A6 and 2.5 ml of aniline.

EXAMPLE 13

The self-doped/grafted polymer of Example 10 above is characterized at microwave frequencies as follows:

The following are loaded into a mixer; a mixture of insulating polymer constituted by 80% polyethylene and 20% EPDM (elastomer), together with 25% by volume of the grafted polymer described in Example 10.

These materials are used to make a centrally-pierced pellet having a diameter of 7 mm and a height of 5 mm. The pellet is positioned in a coaxial waveguide, which is connected to the terminals of a Wiltron 360 type network analyser. The analyzer serves to obtain the wave propagation parameters through the sample considered as a 2-port network. Analysis is performed in the range 40 MHz to 18 GHz and the propagation parameters of the electromagnetic impedance Z of the sample and the propagation constant $\gamma$ through the sample are derived by calculation.

Figure 1:
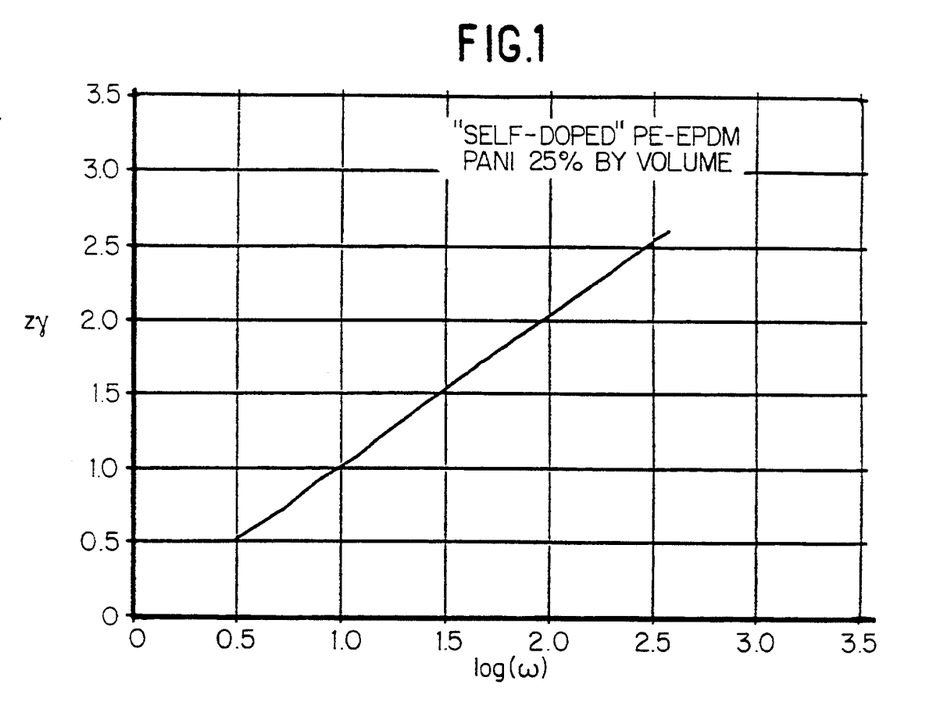
FIGS. 1 and 2 give the parameters $Z\gamma$ and $\gamma/Z$ as a function of the logarithm of the analysis frequency for a polymer of the present invention.
Figure 2:
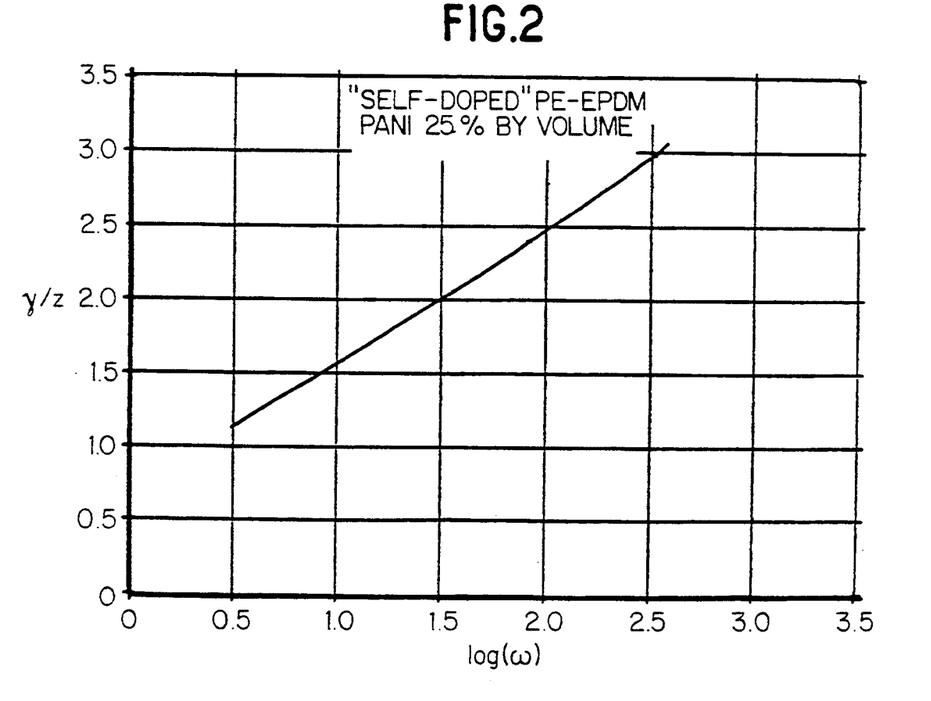

FIGS. 1 and 2 respectively show the parameters $Z\gamma$ and $\gamma/Z$ as a function of the logarithm of the analysis frequency. It can be seen that they are both straight lines over the analysis rage.

Figure 3:
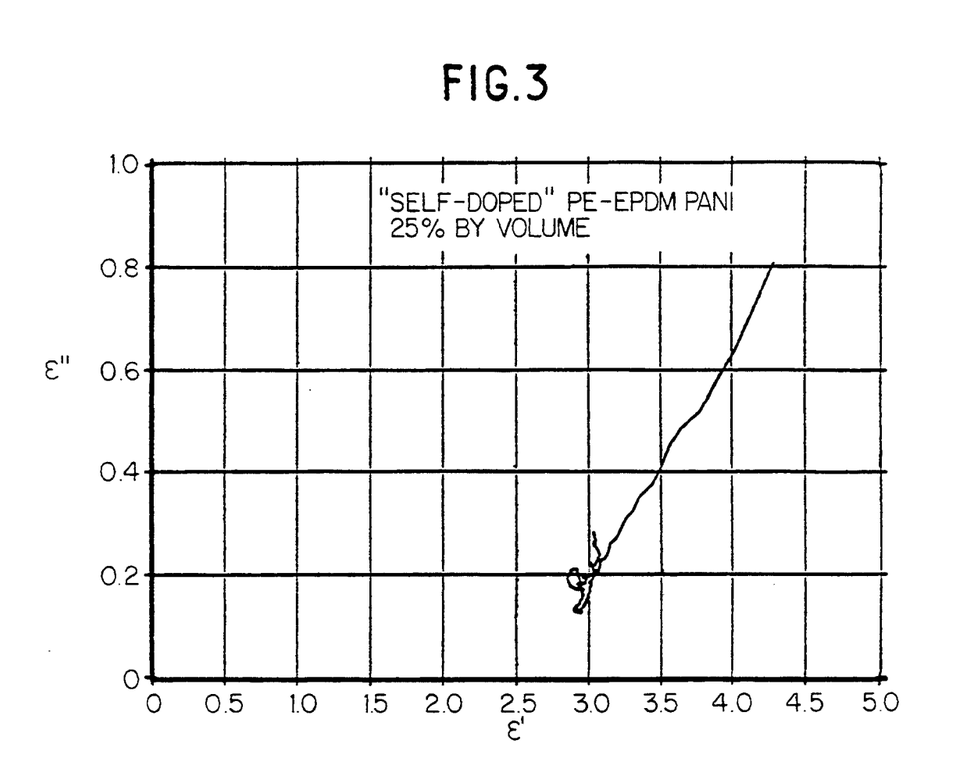
FIG. 3 relates to dielectric constant, being a plot of $\epsilon'/\epsilon''$ for the same polymer.

FIG. 3 relates to the dielectric constant being a complex $\epsilon'/\epsilon''$ plot showing a regression straight line having a slope of about 0.4.

EXAMPLE 14

A 250 cc Erlenmeyer flask contains 1.7 g of aniline, and 5 g of 4-(2-aminophenoxy)-1-butanesulfonic acid in the form of its hydrated sodium salt. These are in solution in 55 ml of water and 20 ml of 96% sulfuric acid. 9.7 g of ammonium peroxodisulfate in solution in 25 ml of water are added drop-by-drop over a period of 3 hours so that the concentration of the medium goes from 9N at the beginning of the reaction to 7N at the end of the reaction. The additional stirring time is chosen to be 1 hour. After centrifuging and washing, the "bottle green" polymer is obtained with a yield of 16%.

Several types of characterization test are then formed on this polymer:

(1) The produce is formed into a pellet without any additive and then the value of its conductivity is obtained by using a 4-point type conductivity measuring method.

Figure 4:
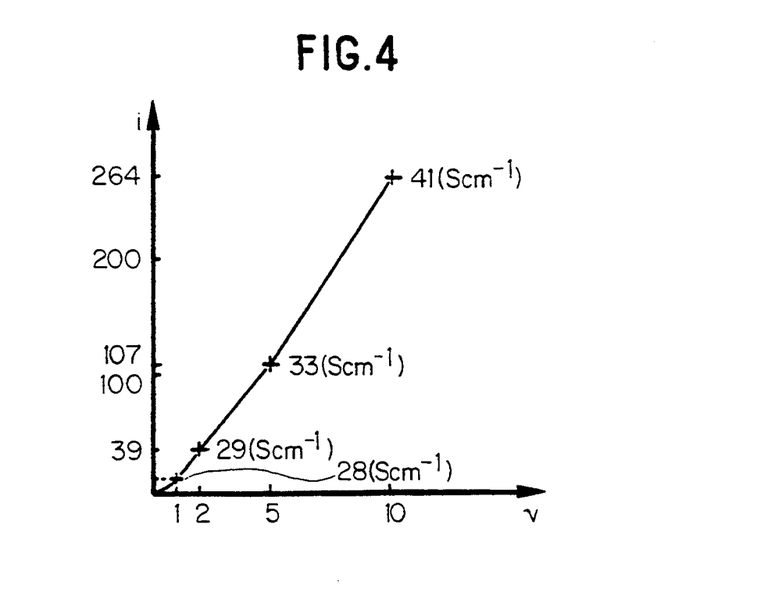
FIG. 4 is a plot of experimental points obtained when measuring low voltage conductivity $\sigma$ for a second polymer of the present invention.

Under such circumstances, it is found that σ lies in the range 30 S.cm$^{-1}$ to 40 S.cm$^{-1}$, which represents excellent conductivity fop a conductive polymer of this type (FIG. 4).

(2) A Debye diagram is made to establish the crystallographic state of the material. The diagram shows that a portion of the material is crystallized, with two diffraction rings being observed at 4.25 Å and 3.59 Å.

EXAMPLE 15

Example 14 is repeated but changing the concentration at the beginning and the end of the reaction respectively to 8N and 5N, by putting 10 ml of sulfuric acid in 30 ml of water. The copolymerization yield is now 26%.

Figure 5:
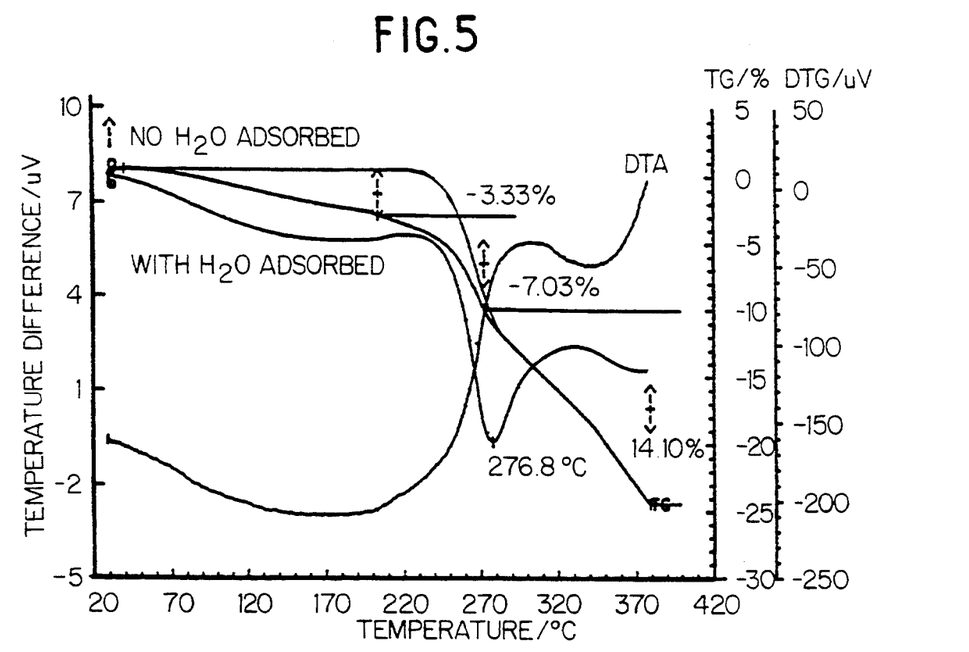
FIGS. 5 and 6 respectively give the results of differential thermal analysis tests and of thermogravimetric analysis tests performed under an atmosphere of nitrogen and argon for a third polymer of the present invention, as defined below in the Example 13.
Figure 6:
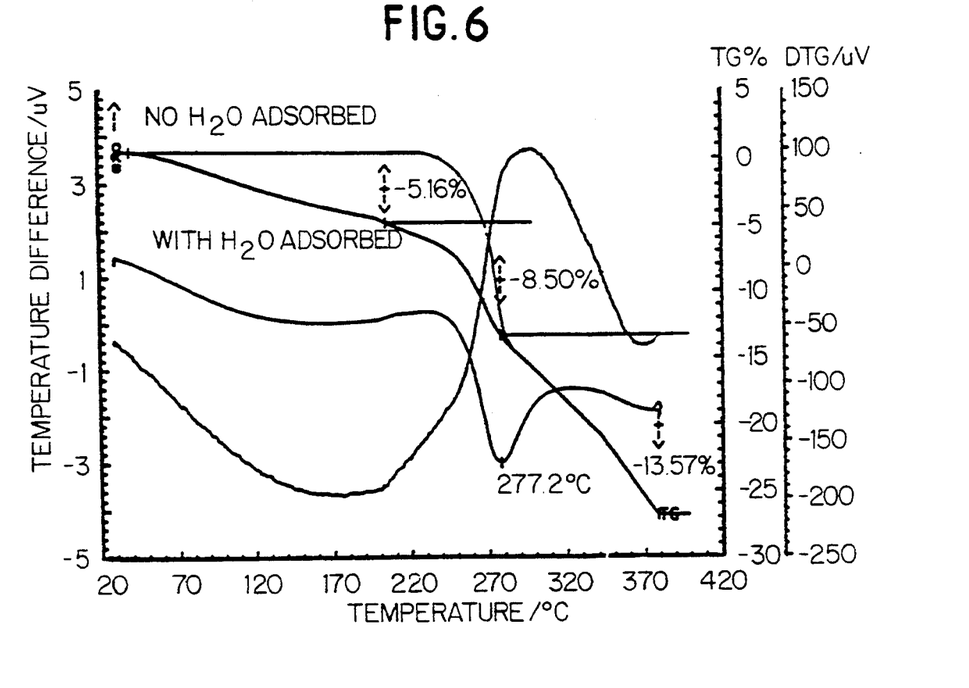

In order to verify the thermal stability of the material, conventional ATD-ATG tests are performed. The results of these tests are given in FIGS. 5 and 6 which show the thermal behavior of the materials when totally dehydrated and when partially dehydrated either under nitrogen and oxygen (FIG. 5), or else under argon (FIG. 6), operating under the following conditions:

|  | FIG. 5 | FIG. 6 |
| --- | --- | --- |
| sample: polyaniline | 99.90 mg | 101.10 mg |
| reference: kaolin | 99.90 mg | 99.80 mg |
| crucible | Al$_2$O$_3$ | Al$_2$O$_3$ |
| TG | 125 mg | 125 mg |

It can be seen that these materials present remarkable thermal stability since they can be heated to about 250° C. without significant mass loss.

EXAMPLE 15

Example 13 is repeated, but to facilitate precipitation, 5 ml of sulfuric acid, 20 ml of water and 40 ml of acetic acid are used. This time, concentration goes from 2.7N to 1.8N respetively at the beginning and at the end of the reaction, and the addition of the solution of ammonium peroxodisulfate lasts for 7 hours. The yield of this reaction is 27%.

EXAMPLE 16

Copolymerization of monomers A3 and B

A3: 3-(2-aminophenoxy)-1-propanesulfonic acid
B: aniline

The oxidizing solution is poured drop-by-drop over 1 night into a thermostated mixture comprising 5 g of monomer A3, 1.66 g of aniline, and 30 ml of 10% by volume sulfuric acid. The polymer is recovered by centrifuging and then the residue is redispersed in a 10% by volume aqueous solution of acetic acid prior to being centrifuged again. This operation which consists in washing the precipitate may be repeated several times. The precipitate is then dried under a vacuum at 50° C. for 2 or 3 days. The yield is calculated relative to the oxidizer, and depending on the oxidizer used, the yield lies in the range 10% to 84%.

Naturally, the present invention is not limited to the particular implementations described and shown, and the person skilled in the art will be capable of making numerous variants without going beyond the ambit of the invention.

We claim:

1. Self-doped conductive polyanilines having a main chain comprising one of benzene and quinone rings, wherein said rings carry grafted chains or substituents represented by the formula:

$$-A-Z$$

in which:

A is a hydrocarbon radical having from 2 to 8 carbon atoms interrupted by at least one hetero atom; and Z is a functional group selected from the group consisting of residues of strong acids and salts thereof.

2. Conductive polyanilines according to claim 1, wherein A is a hydrocarbon radical having from 2 to 8 carbon atoms interrupted by at least one hetero atom selected from the group consisting of O and S.

3. Conductive polyanilines according to claim 1, wherein A is selected from the group consisting of an ether or polyether residue and an ester residue.

4. Conductive polyanilines according to claim 1, wherein A includes an oxygen atom in its chain and is represented by the formula:

$$-(CH_2)_r-O-(CH_2)_s-$$

in which:

r is an integer of 0 or 1; and s is an integer of 3 or 4.

5. Conductive polyanilines according to claim 1, wherein Z is selected from the group consisting of residues of sulfonic, phosphonic, and phosphoric acids and salts thereof.

6. Conductive polyanilines according to claim 1, having a polyemeraldine main chain.

7. Conductive polyanilines according to claim 1, wherein the number of grafted chains represented by —A—Z is equal to one-half the number of benzene and quinone rings constituting the main chain.

8. Conductive polyanilines according to claim 1, wherein the conductivity can be varied by varying the molecular ratio of monomer A to monomer B.

9. A method of preparing conductive polyanilines according to claim 1, comprising the step of copolymerizing two monomers represented by formulae A and B in an acid medium comprising an acid and in the presence of an oxidizer, one of said monomers containing a functional group represented by Z and the other not containing a functional group represented by Z:

in which:

q is 0 or 1;

p is 0 or 1;

$R_1$ and $R_2$ are the same or different and each represents —A—Z in which A is a hydrocarbon radical having from 2 to 8 carbon atoms interrupted by at least 1 hetero atom, and Z is a functional group selected from the group consisting of residues of strong acids and salts thereof;

R and R' are the same or different, with the dashed lines indicating that one or both of R and R' are bonded either to the nitrogen atom or the ring;

when bonded to the ring, R and R' represent —H, —OH, an alkyl radical containing 1 to 12 carbon atoms, —$CH_2OH$, —$C_2H_4OH$, —COOH, —$OCH_3$ or —$OC_2H_5$;

when attached to the nitrogen atom, R and R' represent —H, —OH, an alkyl radical, a phenyl radical, or —COOH;

the copolymerization including an induction stage during which the oxidizer is present in the copolymerization medium, and a production stage.

10. A method according to claim 9, wherein said monomer A is fully present in the reaction medium at the beginning of the reaction, and monomer B and the oxidizer are added in increments or continuously during the period of the induction stage and of the production stage, the fixed ratio of monomer B to oxidizer being constant.

11. A method according to claim 9, wherein said monomer B is also present in the copolymerization medium during the induction stage.

12. A method according to claim 9, wherein said monomers A and B are fully present in the reaction medium at the beginning of the reaction, and the oxidizer is added in increments continuously over the period of the induction stage and of the production stage.

13. A method according to claim 9, wherein the reaction medium is subjected during the induction stage to heating leading to a temperature that may reach 40° C. for several minutes, after which the temperature of the reaction medium is allowed to change under its own inertia.

14. A method according to claim 9, wherein the pH of the reaction medium is less than 1.

15. A method according to claim 9, wherein said acid is selected from the group consisting of hydrochloric acid, sulfuric acid, phosphoric acid, mixtures thereof, and the eutectic HF—$NH_4F$.

16. A method according to claim 9, wherein the oxidizer is selected from the group consisting of $KIO_3$, $H_2O_2$, $(NH_4)_2S_2O_8$ and $(NH_4)_2Cr_2O_7$.

17. A method according to claim 9, characterized in that said monomer B is aniline.

18. A method according to claim 9, wherein said monomer A is aniline mono- or di- substituted on the ring in the ortho position or in the meta position selected from the group consisting of (o)$R_1$-aniline, (m)$R_1$-aniline, (o)$R_1$,(o)$R_2$-aniline, (o)$R_1$,(m)$R_2$-aniline, (m)$R_1$, (o)$R_2$-aniline, (m)$R_1$,(m)$R_2$-aniline, and mixtures thereof.

19. A method according to claim 9, wherein said monomer A is ortho disubstituted aniline.

20. A method according to claim 9, wherein said monomer A contains a functional group selected from the group consisting of residues of sulfonic acid and salts thereof.

21. A method according to claim 9, wherein said monomer A is prepared by the following reaction scheme:

comprising providing an aromatic nitrated compound having at least one hydroxyl or hydroxylated group in the ortho position or the meta position;

preparing a metallic derivative of said compound;

reacting the metal derivative with a sultone in a medium that is anhydrous, polar, and aprotic;

reducing the nitro function into an amino function; and recovering the final product in the form of an internal salt or salt derivative.

22. A method according to claim 9, wherein said monomer A is prepared by the following reaction scheme:

R = H, CH₃, ...
M = Na, K, ...

x = 0, 1, ...

↓ sultone y = 3 or 4 comprising providing an aromatic amine-containing compound having at least one hydroxyl or hydroxylated group in the ortho position or in the meta position; preparing a metallic derivative of said compound; reacting the metal derivative with a sultone in a medium that is anhydrous, polar, and aprotic; and recovering the final product in the form of an internal salt or salt derivative.

* * * * *